United States Patent
Segura-Puchades

(10) Patent No.: US 9,865,764 B2
(45) Date of Patent: Jan. 9, 2018

(54) IMAGE CAPTURE DEVICE WITH INTEGRATED ILLUMINATION AND METHOD FOR PRODUCING THE DEVICE

(71) Applicant: COMMISSARIAT A L'ENERGIE ATOMIQUE ET AUX ENERGIES ALTERNATIVES, Paris (FR)

(72) Inventor: Josep Segura-Puchades, Fontaine (FR)

(73) Assignee: Commissariat A L'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 15/248,176

(22) Filed: Aug. 26, 2016

(65) Prior Publication Data

US 2017/0062643 A1    Mar. 2, 2017

(30) Foreign Application Priority Data

Aug. 28, 2015 (FR) ..................... 15 58025

(51) Int. Cl.
    *H01L 27/146*    (2006.01)
    *G06F 3/042*    (2006.01)
    (Continued)

(52) U.S. Cl.
    CPC ....... *H01L 31/153* (2013.01); *G01N 21/3581* (2013.01); *G06F 3/042* (2013.01); *G06F 3/0412* (2013.01); *G06F 3/0421* (2013.01); *G06K 9/00046* (2013.01); *H01L 27/1469* (2013.01); *H01L 27/14603* (2013.01); *H01L 27/14623* (2013.01); *H01L 27/14625* (2013.01);
    (Continued)

(58) Field of Classification Search
    CPC .......... H01L 27/1469; H01L 27/14603; H01L 27/14623; H01L 27/14625; H01L 27/14634; H01L 27/14636; H01L 27/14658; H01L 27/14678; H01L 27/14685; H01L 33/44; H01L 31/153; G06K 9/00; G06K 9/28; G06K 9/00046; G01N 21/3581; G09G 3/02; G06F 3/042; G06F 3/0421; G06F 3/0412; G06F 3/0428
    USPC ............. 257/80, 81, 432, E31.001, E33.001; 250/208.1, 221; 345/175, 690; 356/612
    See application file for complete search history.

(56) References Cited

U.S. PATENT DOCUMENTS 9,454,265 B2 * 9/2016 Wyrwas ................ G06F 3/0412
9,536,129 B2 * 1/2017 Carver ................. G06K 9/0004
(Continued)

FOREIGN PATENT DOCUMENTS

WO    2006/026796 A1    3/2006

*Primary Examiner* — Dao H Nguyen
(74) *Attorney, Agent, or Firm* — Baker Hostetler LLP

(57) ABSTRACT

An image capture device to produce images of an object in contact with or in immediate proximity to the device comprises a sensor and illumination means capable of emitting a first type of radiation to illuminate an object in order to obtain an image thereof, the sensor comprising pixels that are sensitive to a second type of radiation dependent on the first type of radiation emitted by the illumination means. The sensor is formed on a monolithic substrate comprising multiple passages that are transparent to the first type of radiation. The illumination means comprise at least one source of the first type of radiation positioned so as to face one of the passages. The invention also relates to a method for producing this device.

13 Claims, 7 Drawing Sheets

(51) Int. Cl.
*G06K 9/28* (2006.01)
*H01L 31/153* (2006.01)
*H01L 33/44* (2010.01)
*G06F 3/041* (2006.01)
*G01N 21/3581* (2014.01)
*G06K 9/00* (2006.01)

(52) U.S. Cl.
CPC .. *H01L 27/14634* (2013.01); *H01L 27/14636* (2013.01); *H01L 27/14658* (2013.01); *H01L 27/14676* (2013.01); *H01L 27/14678* (2013.01); *H01L 27/14685* (2013.01); *H01L 33/44* (2013.01)

(56) References Cited

U.S. PATENT DOCUMENTS

| | | | |
|---|---|---|---|
| 2007/0292307 A1 | 12/2007 | Padinger et al. | |
| 2008/0074401 A1* | 3/2008 | Chung | G02F 1/1368 345/175 |
| 2013/0119237 A1* | 5/2013 | Raguin | H01L 27/14601 250/208.1 |
| 2013/0120760 A1* | 5/2013 | Raguin | G01B 11/24 356/612 |
| 2015/0015544 A1* | 1/2015 | Kim | G06F 3/0418 345/175 |
| 2015/0084928 A1* | 3/2015 | Wyrwas | G06F 3/0421 345/175 |
| 2015/0084994 A1* | 3/2015 | Wyrwas | G09G 3/02 345/690 |

* cited by examiner

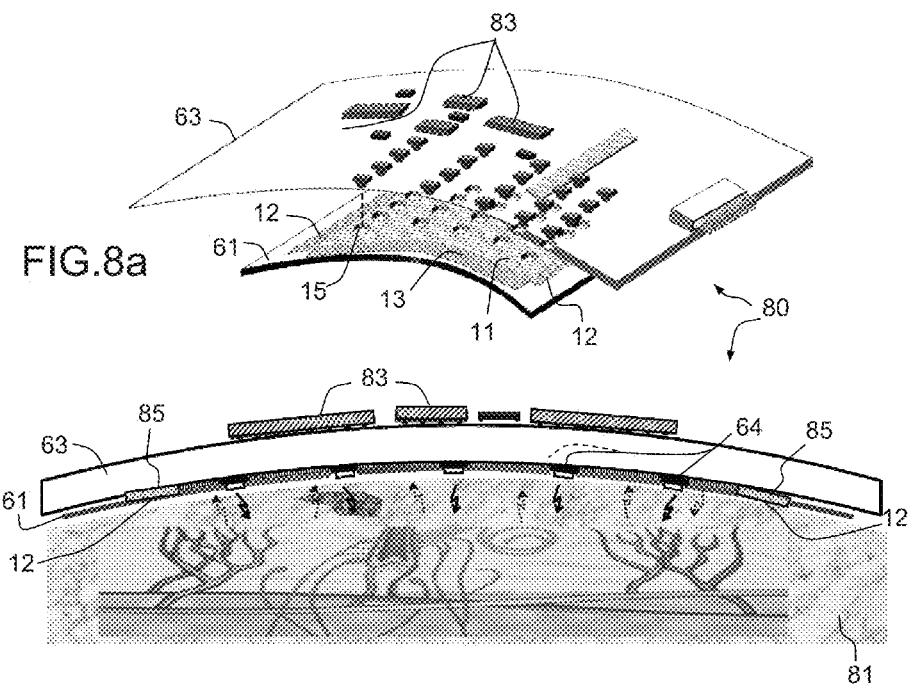
FIG.8a
FIG.8b
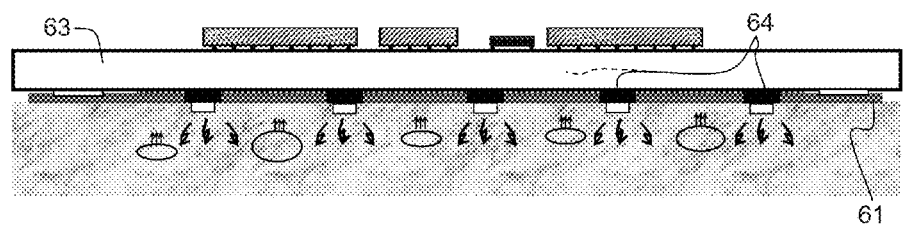
FIG.9

IMAGE CAPTURE DEVICE WITH INTEGRATED ILLUMINATION AND METHOD FOR PRODUCING THE DEVICE

CROSS-REFERENCE TO RELATED APPLICATIONS

This application claims priority to foreign French patent application No. FR 1558025, filed on Aug. 28, 2015, the disclosure of which is incorporated by reference in its entirety.

FIELD OF THE INVENTION

BACKGROUND OF THE INVENTION

The invention relates to an image capture device intended to produce images of an object in contact with or in immediate proximity to the device. The invention also relates to a method for producing this device. This type of device may be employed in numerous fields, such as in medical imaging in order to produce images of living tissues, in the recognition of persons, e.g. for fingerprint sensors, in the inspection of materials, etc.

BACKGROUND

The production of an image requires a sensor having multiple elements that are sensitive to a type of radiation. These sensitive elements are called pixels and are generally arranged in a matrix. Each pixel delivers a signal that is representative of the radiation it receives. A set of signals originating from the various pixels allows a two-dimensional image to be formed whose dimensions are dependent on the number and arrangement of the pixels in the matrix.

In the context of the invention, the radiation to which the sensor is sensitive may be of any type, such as, for example, electromagnetic radiation any frequency of which, from ionizing gamma or X-ray radiation to terahertz radiation, may be employed.

The pixels receive radiation arising from an object that it is desired to image. This radiation may be reflected by the object or arise from stimulation, such as, for example, in the case of fluorescence. In order to obtain this reflection or this stimulation, a source of incident radiation is required. When the image capture device is in immediate proximity to the object that is desired to be imaged, the source is advantageously integrated into the device. The invention more particularly pertains to devices with integrated sources.

In devices of small size, it is possible to place the source of incident radiation on the periphery of the sensor. In order to make the illumination uniform, it is possible to position multiple point sources around the sensor. However, this arrangement does not allow completely uniform illumination to be obtained. Specifically, the pixels located in the center of the sensor are much further away from the light sources than the pixels located on the periphery and the differences in illumination may be detrimental to the image arising from a sensor configured in this way.

In order to bring the pixels closer to the light source, it is also possible to decrease the size of the sensor. To produce an image of large size, it is then possible to juxtapose multiple sensors while leaving an interstice between the sensors. A light source may then be positioned in the interstice. The presence of multiple sensors leads to difficulties in positioning the sensors with respect to one another in order to align them. The number of sensors and the difficulties in positioning tend to increase the cost of the device.

The production of a sensor that is partially transparent to the radiation from the source of incident radiation has also been attempted, such as, for example, described in document US 2013/119237 A1. More specifically, the sensor may be transparent between the pixels. The source of radiation is not a point source. It extends over the entire surface of the sensor. This embodiment nonetheless has multiple drawbacks:

The fill factor of the sensor must be reduced in order to provide enough space for the radiation to pass between the pixels. Stated otherwise, the useful area of the pixels must be decreased, thereby negatively affecting the sensitivity of the device.

The radiation passing through the sensor may be directly detected by the light-sensitive elements of the pixels, which is undesirable.

The cost of such a device increases in proportion to the difficulty of producing a distributed source of radiation and the need to protect the pixels from radiation arising directly from the source.

Even if the radiation arising from the source is not directly detected by the sensitive elements, parasitic currents may be generated by light in components, such as transistors, present in each of the pixels in addition to the sensitive element.

Another, older alternative is described in document US 2007/292307 A1. It consists in positioning light-sensitive elements and light-emitting diodes on one and the same substrate. In practice, this architecture requires tracks to be shared by the light-sensitive elements and light-emitting diodes and, at the present time, no such technology for implementing this device is available at a reasonable cost. Moreover, it is difficult to achieve, on one and the same substrate, commands that are differentiated by the light-sensitive elements and light-emitting diodes.

SUMMARY OF THE INVENTION

The invention aims to overcome all or some of the problems mentioned above by proposing a low-cost image capture device whose sensor is monolithic.

To this end, one subject of the invention is an image capture device comprising a sensor and illumination means capable of emitting a first type of radiation intended to illuminate an object in order to obtain an image thereof, the sensor comprising pixels that are sensitive to a second type of radiation dependent on the first type of radiation emitted by the illumination means, the pixels being arranged in a matrix, characterized in that the sensor is formed on a first monolithic substrate comprising multiple passages that are transparent to the first type of radiation, each of the passages occupying the position of at least one pixel missing from the matrix arrangement, in that the illumination means comprise a second substrate parallel to the first substrate and bearing multiple sources of the first type of radiation, and in that one of the sources of the first type of radiation is positioned so as to face each of the passages.

Each of the passages may occupy the position of multiple contiguous pixels.

The passages are advantageously uniformly distributed across the matrix arrangement in order to improve the uniformity of the illumination of the object.

The pixels that are contiguous with the passages may be inactive. The neutralization of these pixels is advantageous, for example for passing control conductors or conductors for the readout of other pixels therethrough.

The device may comprise components allowing the pixels to be controlled and read out. The sensor then comprises tracks connecting each of the pixels to the components, each track being routed along a row of pixels. For the rows interrupted by passages, the corresponding tracks may be diverted around the passages via neighboring, uninterrupted rows.

The substrate comprises a front face bearing the pixels, and a rear face opposite the front face. The sensor may comprise a mask that is opaque to the first type of radiation, the mask being positioned on the rear face.

The first substrate and the second substrate are advantageously flexible, for example in order to closely follow the shape of the object.

The second substrate comprises a front face positioned so as to face the sensor. The illumination means may comprise a mask that is opaque to the radiation emitted by the at least one source of the first type of radiation, the mask being positioned on the front face, the mask of the illumination means being apertured facing the passages.

The at least one source of the first type of radiation may be positioned away from the sensor or in contact therewith.

Each of the passages may be an aperture passing through the first substrate or a transparent zone of the first substrate.

Another subject of the invention is a method for producing a device according to one of the preceding claims, characterized in that it comprises the following steps:
  producing the sensor from the first substrate;
  producing the illumination means from the second substrate;
  then assembling the sensor and the illumination means.

BRIEF DESCRIPTION OF THE FIGURES

The invention will be better understood and further advantages will become apparent upon reading the detailed description of one embodiment given by way of example, which description is illustrated by the attached drawing in which:

FIGS. 8a and 8b show an exemplary device according to the invention employed in biomedical analysis;

FIG. 9 shows another exemplary device employed in material analysis;

For the sake of clarity, the same elements have been given the same references in the various figures.

DETAILED DESCRIPTION OF THE INVENTION

Figure 1:
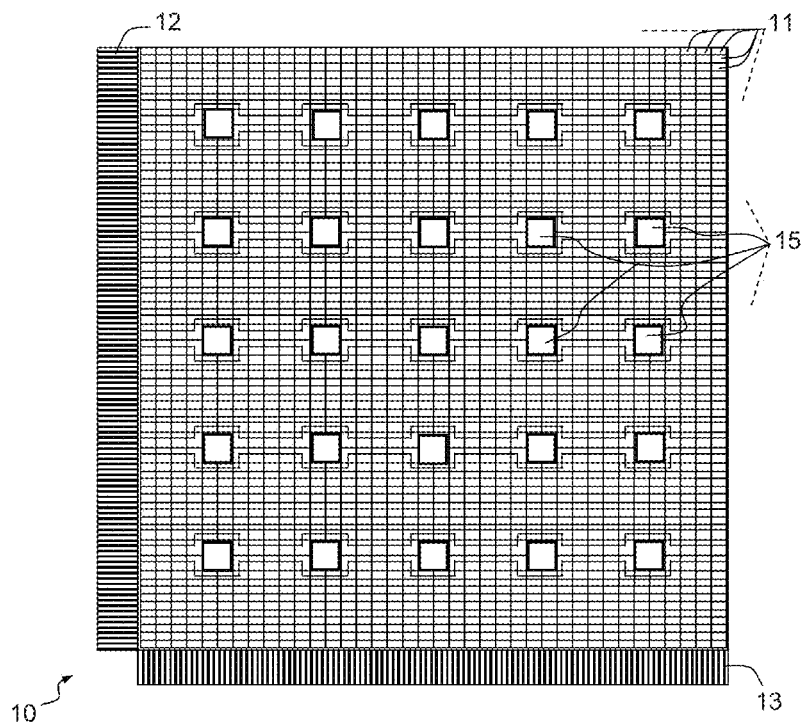
FIG. 1 shows an exemplary sensor that may be employed in a device according to the invention.

FIG. 1 shows a sensor 10 formed on a monolithic substrate. The sensor 10 comprises pixels 11 that are sensitive to a type of radiation, for example electromagnetic radiation. The pixels 11 are, in the example shown, regularly distributed across the surface of the sensor 10. The pixels are arranged in a matrix formed from rows and columns of pixels 11. Other, irregular arrangements are also possible within the scope of the invention. In FIG. 1, each pixel takes the form of a square. The pixels 11 are considered to be contiguous. In practice, a pixel comprises an element that is sensitive to the radiation and generally one or more components, required for the operation of the pixel, such as e.g. one or more transistors. In each of the squares shown in FIG. 1, a sensitive element and the one or more associated components are positioned. Within the area of a square, tracks allowing signals to be conveyed to or from each pixel may also be found. On the periphery of the sensor, on the substrate, specific components, distributed in two zones 12 and 13, are provided. These components allow, in particular, the matrix of pixels 11 to be controlled and read out. The specific components may be transferred to another substrate. The zones 12 and 13 then form zones for the connection of the pixels 11 to the transferred specific components. In the example shown, two zones are visible. It is also possible to produce these sensors with another number of zones.

According to the invention, the sensor comprises multiple passages 15 that are each intended to allow a type of radiation arising from a source of radiation to pass therethrough. Each of the passages 15 occupies the position of at least one pixel 11 of the matrix arrangement. Stated otherwise, at least one missing pixel forms a passage 15. The passages 15 may be apertures passing through the substrate of the sensor 10 such as, for example, drill holes made in the substrate. Alternatively, it is possible to retain a continuous planar substrate. The passages 15 are then produced in the form of transparent zones of the substrate. The passages may occupy the position of a single pixel or of multiple contiguous pixels 11. In the example shown, each passage 15 occupies a square of two by two pixels. Other dimensions are possible. It is particularly possible to envisage squares of larger size, or even rectangles (a different number of pixels in the two directions of the matrix). The dimensions of the passages are chosen according to those of the retained sources of incident radiation. The passages 15 are throughholes and allow sources of incident radiation, intended to illuminate an object that it is desired to image by means of the sensor 10, to be positioned therein.

In order to obtain good uniformity of illumination from the sources of incident radiation, the passages 15 are advantageously uniformly distributed across the matrix of pixels. More specifically, the number of pixels 11 separating two neighboring passages 15 is identical for all pairs of neighboring passages, and this is the case in both directions of the matrix.

Each pixel 11 delivers information that depends on radiation arising from the object illuminated either via reflection of the radiation incident on the object or via stimulation of the object by the incident radiation. Throughout the remainder of the document, the incident radiation emitted by the sources that are intended to illuminate the object will be referred to as the first type of radiation and the radiation arising from the object will be referred to as the second type of radiation.

In the sensor 10, level with each passage 15, pixels are missing. In order to obtain a complete image of the object, it is possible to carry out processing in order to reconstruct the information that would have come from the missing pixels, for example by averaging information arising from neighboring pixels 11.

Figure 2A:
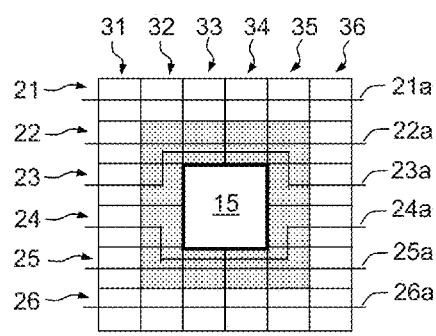
FIGS. 2a and 2b more specifically show, around a passage of the sensor of FIG. 1, the routing of conductors allowing the pixels of the sensor to be controlled.
Figure 2B:
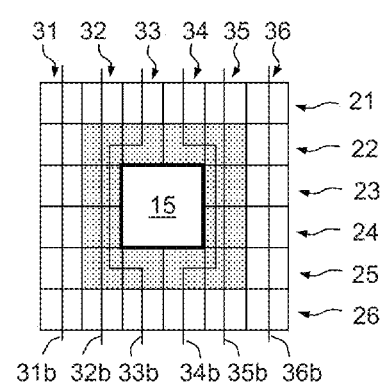

FIGS. 2a and 2b partially show the sensor 10 around a passage 15. The various pixels 11 of the matrix are connected to the zones 12 and 13 by tracks. For example, the zone 12 may be used to control the pixels. Each row of pixels 11 is connected by one or more tracks to the zone 12. It is, for example, possible to envisage two tracks per row of pixels 11, one track allowing the pixels 11 to be reset and another track allowing the row of pixels to be selected. Likewise, each column of pixels 11 is connected by one or more tracks to the zone 13. For each column, one track may connect the pixels 11 of the column to a readout circuit located in the zone 13. Other tracks may be provided in rows or in columns in order to supply the pixels with power.

In FIG. 2a, a single track per row of pixels 11 is shown so as not to overload the figure. Likewise, in FIG. 2b, a single track per column of pixels 11 is shown. When multiple tracks are required per row or per column, they follow parallel routes. In order to allow the tracks arranged in rows and in columns to cross, they may be positioned in different layers of the substrate, which layers are separated by an insulator.

In FIGS. 2a and 2b, six rows denoted by 21 to 26 and six columns of pixels denoted by 31 to 36 are shown. In FIG. 2a, for each row, the track shown is denoted by the reference of the corresponding row followed by the letter "a". Likewise, in FIG. 2b, for each column, the track shown is denoted by the reference of the corresponding column followed by the letter "b". Rows 21, 22, 25 and 26 are not interrupted by a passage 15 and the corresponding tracks 21a, 22a, 25a and 26a follow the pixels 11 of their respective row. On the other hand, for rows 23 and 24, pixels are missing at columns 33 and 34. These four missing pixels form the passage 15. The routing of tracks 23a and 24a is diverted into the pixels located in the vicinity of the passage 15 by following the closest uninterrupted row of pixels. More specifically, track 23a is diverted via the pixels of row 22 and track 24a is diverted via the pixels of row 25 in the vicinity of the passage 15.

Likewise, the routing of tracks 33b and 34b is diverted into the pixels located in the vicinity of the passage 15 by following the closest uninterrupted column of pixels. More specifically, track 33b is diverted via the pixels of column 32 and track 34b is diverted via the pixels of column 35 in the vicinity of the passage 15.

The pixels that are contiguous with the passages 15 are advantageously inactive, mainly due to the particular routing of the diverted tracks passing through these pixels. In FIGS. 2a and 2b, these pixels located on the periphery of the passage 15 are shown in gray. Specifically, these pixels may receive the first type of radiation directly, without reflection off the object. Stated otherwise, these pixels may be dazzled by the source of radiation passing through the pixel 11. The information that they deliver may be erroneous. In order to deactivate them, it is possible to remove the sensitive element contained therein, thereby facilitating the routing of the diverted tracks. Alternatively, it is possible to retain the same pattern for all pixels, whether active or inactive. The inactive pixels therefore each retain a sensitive element which may be connected to the zones 12 and 13 as is the case for the other pixels. It is envisaged to process the image in order to ignore the information received from the pixels 11 that are contiguous with the passages 15. As is the case for the missing pixels, the image may be reconstructed from the active neighboring pixels 11.

Alternatively, in the case of a continuous substrate comprising transparent zones forming the passages 15, it is possible to avoid diverting any tracks for the purpose of circumventing the passages 15. More specifically, at each passage 15, for each missing pixel, the light-sensitive element normally provided in the matrix arrangement is missing and the components required for the operation of the pixel are potentially also missing. Only the tracks provided in rows and in columns remain, these tracks passing through the corresponding passage in a straight line without changing direction at the passage 15. The tracks passing through the passages may be opaque to the radiation arising from the source of radiation. The radiation arising from the source passes through the substrate via zones freed by the absence of light-sensitive elements and components required for the operation of the missing pixel. Advantageously, it is possible to form these tracks by means of conductors that are transparent to the radiation arising from the source. It is possible, for example, to employ transparent conductive oxides or TCOs. Certain oxides of metal alloys, such as indium tin oxide (or ITO) are also known for allowing the production of transparent conductors.

Figure 3:
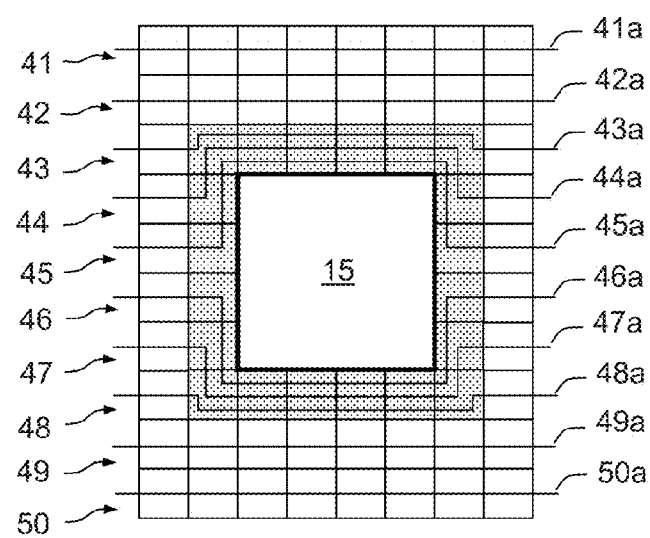
FIG. 3 shows, still around a passage, a sensor variant in which the passage is larger than that shown in FIGS. 2a and 2b.

FIG. 3 shows a sensor variant in which the passage 15 is larger than that shown in FIGS. 2a and 2b. The passage shown in FIG. 3 occupies an area of four pixels by four pixels. Ten rows denoted by 41 to 50 are shown. As above, for each row, the track shown is denoted by the reference of the corresponding row followed by the letter "a".

Rows 41, 42, 43, 48, 49 and 50 are not interrupted by a passage 15 and the corresponding tracks 41a, 42a, 43a, 48a, 49a and 50a follow the pixels 11 of their respective row. On the other hand, for rows 44, 45, 46 and 47, pixels are missing in order to form the passage 15. The routing of tracks 44a, 45a, 46a and 47a is diverted into the pixels located in the vicinity of the passage 15 by following the closest uninterrupted row of pixels. More specifically, tracks 44a and 45a are diverted via the pixels of row 43 and tracks 46a and 47a are diverted via the pixels of row 48 in the vicinity of the passage 15. In this variant, three tracks follow the pixels of row 43 and three tracks follow the pixels of row 48 in order to circumvent the passage 15. The same type of diversion in the vicinity of the passage 15 is made by the tracks passing through the columns of pixels.

Alternatively, it is possible to decrease the number of tracks passing through one and the same row of pixels by routing, for example, a maximum of only two tracks per row of pixels, by routing only tracks 44a and 45a through row 43. Track 43a is diverted via row 42 even though it includes no missing pixels. Thus, two tracks follow row 43 and two tracks follow row 42. This arrangement allows a track width and a distance between neighboring tracks that is more substantial than in the variant shown in FIG. 3 to be obtained. It is possible to deactivate all pixels through which diverted tracks pass.

Figure 4:
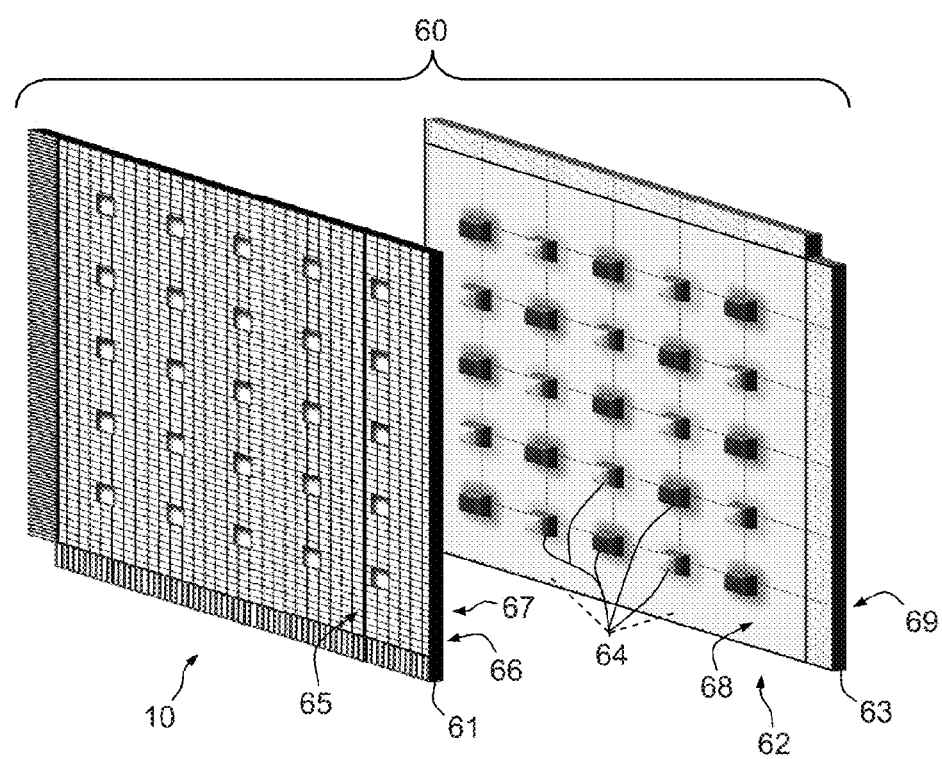
FIG. 4 shows an exploded view of a device according to the invention.

FIG. 4 shows an exploded view of an image capture device 60 comprising the sensor 10 produced on a substrate 61. The device 60 comprises means 62 for illuminating an object that it is desired to image. The illumination means comprise a substrate 63 and sources 64 of the first type of radiation. The two substrates 61 and 63 are, for example, placed in contact with one another. The first type of radiation passes through the passages 15 produced in the substrate 61. It is advantageous to have two different substrates, 61 and 63, one for the sensor 10 and the other for the illumination means 62 in order to clearly separate the function of the sensor 10, which is to bear the pixels, and that of the illumination means 62, which is to illuminate the object. It is possible to place a mask 67 that is opaque to the first type of radiation on a rear face 66 of the sensor 10, which face is opposite a front face 65 of the sensor 10 bearing the sensitive elements, in order to protect the components of the sensor from all direct illumination arising from the illumination means 62. The mask 67 may cover the entirety of the rear face 66. The mask 67 is interrupted by the passages 15. The substrate 61 may be made of a material that is transparent to the radiation arising from the illumination means 62, such as, for example, glass or a transparent plastic material.

The illumination means 62 may be formed from a source of radiation that is uniformly distributed across the entire surface of the sensor 10. However, a high level of uniformity of illumination from this type of source is tricky to achieve. The illumination may in particular be weaker in the center of the sensor 10. Advantageously, separate sources 64 are positioned so as to face the passages 15. Stated otherwise, a source 64 is positioned so as to face each of the passages 15. The sources 64 may be formed from light-emitting diodes forming sources that are almost point sources. More specifically, the dimensions of each source 64 are substantially equal to those of the passage 15 that it is facing. It is advantageous that the dimensions of each source 64 are smaller than or equal to the dimensions of the passage 15 that it is facing, so as to limit the illumination of the pixels 11 adjoining the passage 15 by the radiation arising from the source 64. The sources 64 are mounted on a front face 68 of the substrate 63 making contact with the rear face 66 of the sensor 10. The sources 64 may protrude with respect to the front face 68 and each may be inserted into one of the passages 15. The illumination means 62 may comprise other components, in particular for the operation of the sources 64. By way of example, these may be resistors for biasing the light-emitting diodes that are used as sources 64 or else selection transistors. In general, these other components are advantageously positioned on a rear face 69 of the substrate 63, the rear face 69 is opposite the front face 68.

Figure 5A:
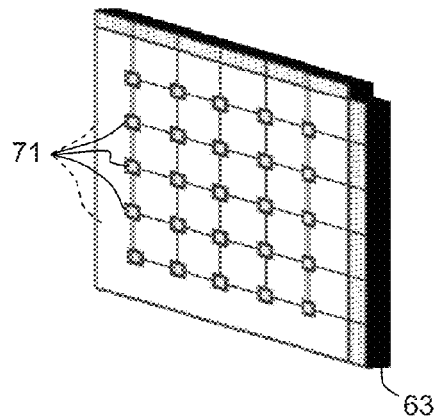
FIGS. 5a to 5d show multiple variant embodiments of illumination means employed in a device according to the invention.
Figure 5B:
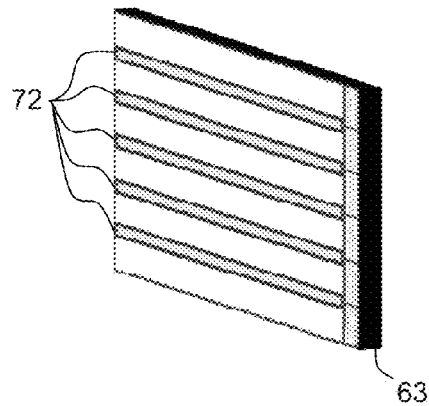
Figure 5C:
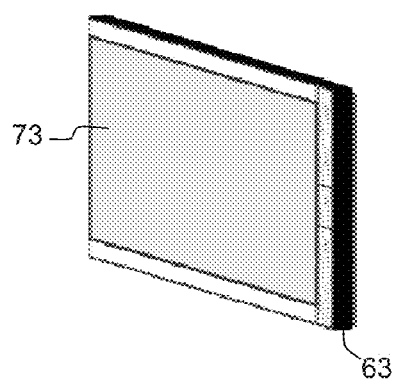
Figure 5D:
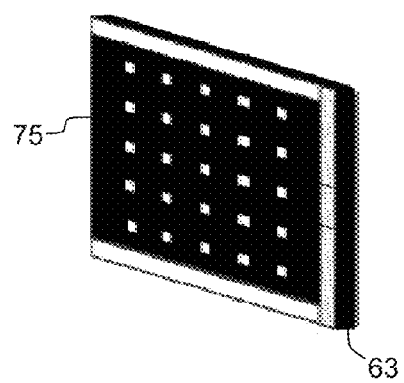

FIGS. 5a to 5d show multiple variant embodiments of the illumination means 62 employing organic light-emitting diodes, in particular polymer light-emitting diodes or PLEDs. Certain polymers employed in this type of diode remain in liquid form. They may be deposited in a thin layer without requiring vacuum deposition. The substrate 63 may be flexible. In FIG. 5a, multiple independent diodes 71 are deposited on the substrate 63 and, more specifically, on its front face 68. The distribution of the diodes 71 on the substrate 63 corresponds to the distribution of the passages 15 on the substrate 61. The diodes 71 may be controlled individually or in groups. In FIG. 5b, diodes 72 are produced in rows, each corresponding to a row of passages 15. In FIG. 5c, a single diode 73 occupies the entire surface of the substrate 63. FIG. 5d reuses the distribution of the diodes 71, 72 or 73. A mask 75 that is opaque to the radiation emitted by the diodes has been added to the front face 68. The mask 75 is apertured facing the passages 15.

Figure 6A:
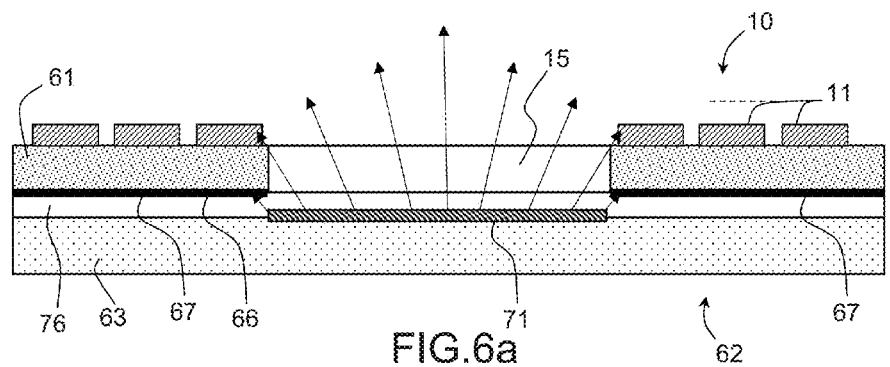
FIGS. 6a, 6b and 6c show, in cross section, multiple variants of devices according to the invention.
Figure 6B:
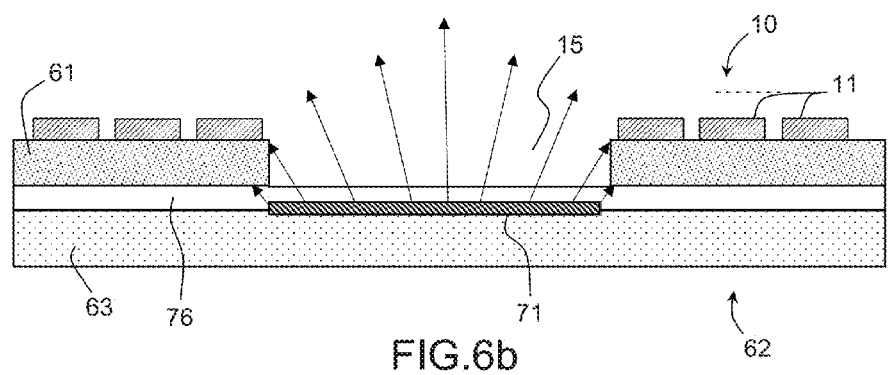
Figure 6C:
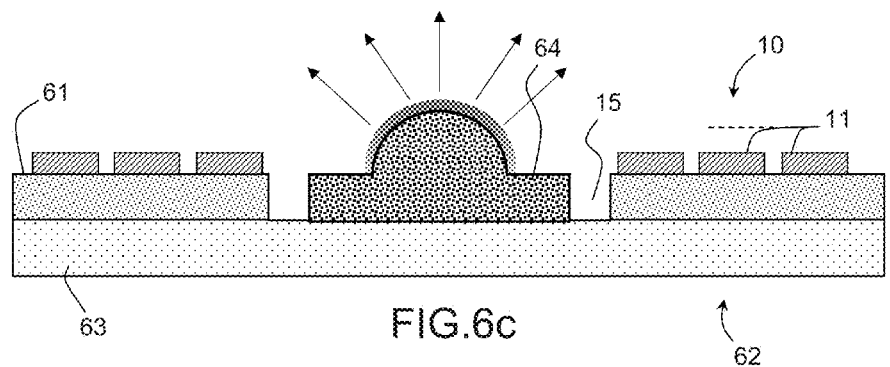

FIGS. 6a, 6b and 6c show, in partial cross section, multiple variants of devices according to the invention. The sensor 10 and the illumination means 62 are shown. The cross sections are shown in a plane that is perpendicular to the plane of the sensor 10, level with one of the passages 15 and the pixels 11 surrounding it. In the variants of FIGS. 6a and 6b, the illumination means 62 comprise, facing each passage 15, an organic light-emitting diode 71 produced on the substrate 63. A transparent encapsulation layer 76 may cover the entirety of the substrate 63, including the diode 71. In the variant of FIG. 6a, the substrate 61 of the sensor 10 is transparent to the radiation emitted by the diode 71. The substrate 61 is not interrupted in order to form the passage 15. The radiation emitted by the diode 71 passes through the substrate 61. A mask 67 is advantageously positioned on the rear face 66 of the sensor 10. Even in the absence of mask 67, the fact that the diodes 71 are positioned only so as to face the passages 15 nonetheless prevents the radiation emitted by the illumination means 62 from interfering with the pixels 11. In this variant, certain pixels 11 adjoining the passage 15 may still receive a portion of the radiation emitted by the diode 71 due to it passing through the substrate 61. The mask 67 allows this interference to be limited but not to be completely eliminated.

In the variant of FIG. 6b, the substrate 61 of the sensor 10 is opaque to the radiation emitted by the diode 71. The substrate 61 is interrupted in order to form the passage 15. In this variant, the pixels 11 adjoining the passage 15 are better protected from the radiation emitted by the diode 71.

In the variant of FIG. 6c, the sources 64 are, for example, light-emitting diodes surface-mounted on the substrate 63. The substrate 61 of the sensor 10 is also interrupted at the passage 15. The light-emitting diode 64 is situated inside the passage 15.

Figure 7:
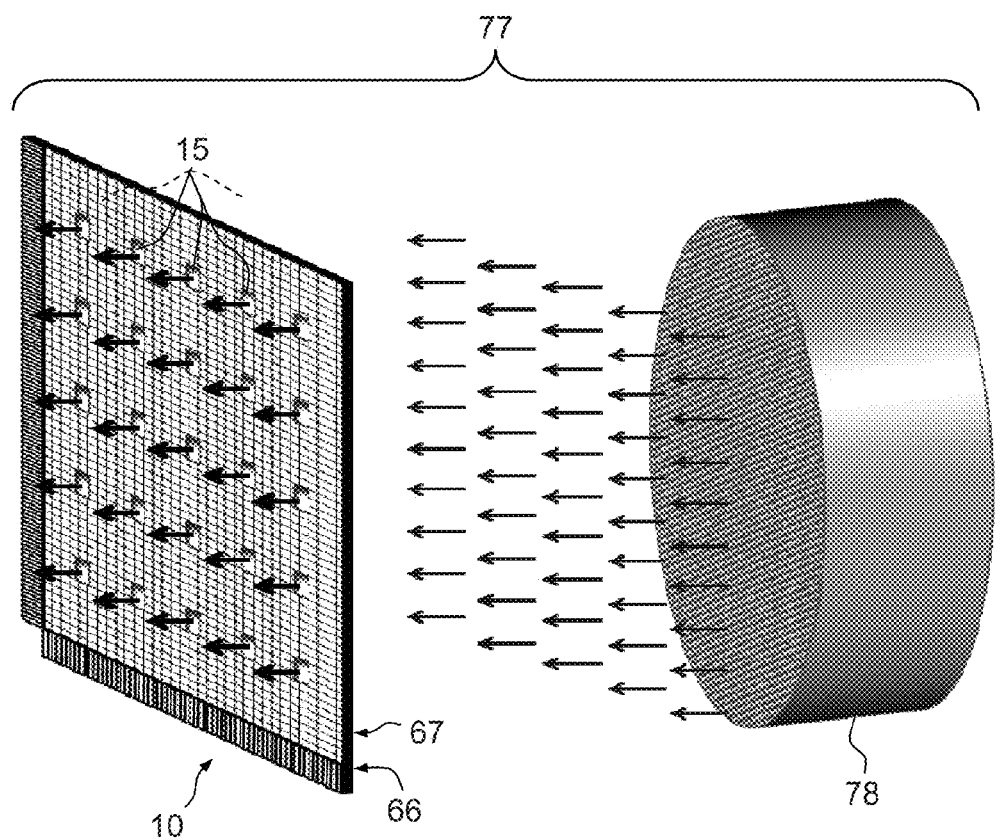
FIG. 7 shows an exploded view of another device according to the invention.

FIG. 7 shows another embodiment of an image capture device 77 similar to the device 60 shown in FIG. 4. The device 77 is suited to X-ray or terahertz radiation imaging. Terahertz radiation is sometimes called far infrared radiation. It is located in a frequency band between the near infrared and microwaves, typically between 0.1 and 10 terahertz. Terahertz radiation may be used in the fields of medical diagnosis, non-destructive testing or security.

The sensor 10 is also located in the device 77. The illumination means bear the reference 78 in this instance. It is a source emitting radiation in the adopted frequency band. The source 78 is positioned a distance away from the sensor 10 on the rear face 66 side. The sensor 10 also comprises a mask 67 that is opaque to the radiation arising from the source 78. As in the device 60, the radiation arising from the source 77 passes through the passages 15 in order to illuminate an object that it is desired to image.

FIGS. 8a and 8b show an exemplary image capture device 80 employed in biomedical analysis. The device 80 is brought into contact with the skin 81 of a patient, for example, in order to detect tumors or to locate veins and arteries. The two substrates 61 and 63 are flexible, making the device 80 flexible so that it is able to closely follow the surface of the skin 81. The zones 12 and 13 form zones for the connection of the pixels 11 positioned on the substrate 61 to the components 83 positioned on the substrate 63. The components 83 allow the sources 64 and, potentially, the pixels 11 to be controlled and read out. The substrate 63 also comprises connection zones 85 that make contact with the connection zones 12 and 13 in order to allow electrical contact between them. The sources 64 are, for example, infrared emitters and the pixels 11 are sensitive to the infrared radiation that is re-emitted differently depending on the biological nature of the tissues of the skin 81.

FIG. 9 shows another exemplary image capture device employed in material analysis. The device of FIG. 7 may be likened to the device 80 of FIGS. 6a and 6b. Both substrates 61 and 63 are shown. The substrate 61 is drilled in order to allow the sources 64 to pass through. For material analysis, the sources 64 may, for example, be sources of visible light that may or may not be lasers, hot spots produced via heating resistors, X-ray emitters, etc. In practice, any form of source that is substantially a point source may be used in order to illuminate the object that is desired to be imaged.

Figure 10:
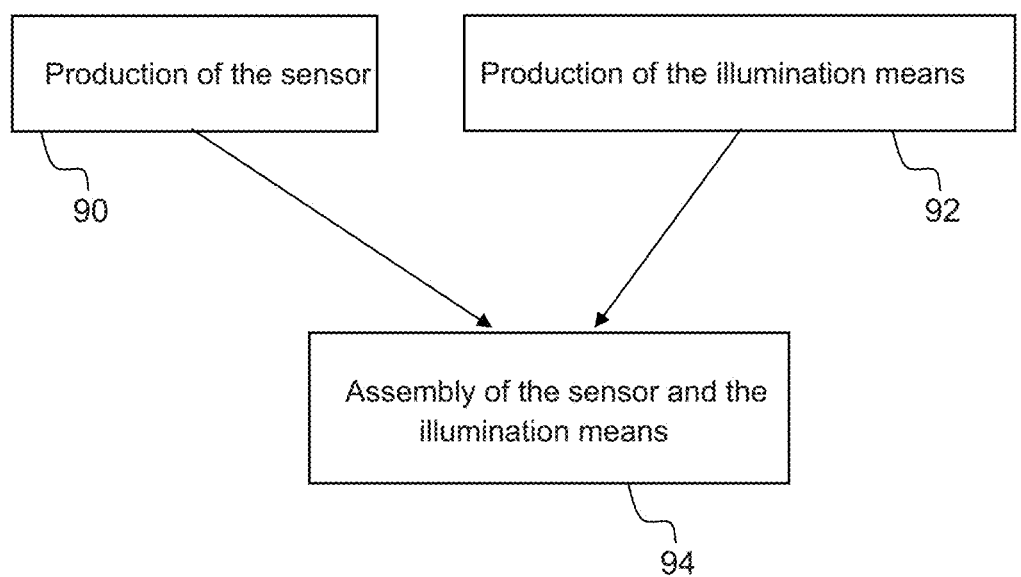
FIG. 10 shows steps in the production of a device according to the invention.

FIG. 10 shows various steps in the production of a device according to the invention. A step 90 shows the production of the sensor 10 from its substrate 61. Conductive tracks used for supplying power to, controlling and reading out the various pixels 11 of the sensor 10 are, for example, etched on the substrate 61. The components of the pixels, light-sensitive elements and other components are, for example, added to the substrate 61. It is also possible to produce the sensor in thin layers deposited on the substrate 61 by employing a photolithography process.

A step 92 shows the production of the illumination means 62 from its substrate 63. As for the sensor 10, the tracks required for supplying the sources 64 with power may be etched on the substrate 63, while the sources 64 may be surface-mounted on the substrate 63. The sources 64 then protrude with respect to the plane of the substrate 63. For the variants described with reference to FIGS. 6a and 6b, the sources are organic light-emitting diodes 71 produced, for example, in thin layers on the substrate 63. It is advantageous to separate the production of the sensor 10 and of the illumination means 62 due to the different natures of the light-sensitive elements of the sensor 10 and the sources 64 of the illumination means 62, in particular when produced in thin layers.

A step 94 shows the assembly of the sensor 10 and the illumination means 62 once they have been produced. If the two elements to be assembled are produced in thin layers, their thickness is substantially constant and the assembly may be achieved by adhesive bonding. The adhesive employed is transparent to the radiation emitted by the illumination means 62. The adhesive is, for example, deposited in the form of a film. The sensor 10 is subsequently pressed against the illumination means 62. Alternatively, in the variant of FIG. 6c, during the assembly of the sensor 10 and the illumination means 62, the light-emitting diodes 64 are fitted into the passages 15 of the sensor 10. Still referring to the variant of FIG. 6c, the illumination means 62 may be adhesively bonded to the sensor 10 and the adhesive used for this assembly does not have to be transparent.

The invention claimed is:

1. An image capture device comprising:
   a sensor; and
   an illumination means configured to emit a first type of radiation to illuminate an object in order to obtain an image thereof,
   wherein the sensor comprises pixels that are sensitive to a second type of radiation dependent on the first type of radiation emitted by the illumination means, the pixels being arranged in an incomplete matrix having positions of at least one missing pixel, and the sensor is formed on a first monolithic substrate comprising multiple passages that are transparent to the first type of radiation, each of the passages occupying the position of at least one missing pixel, and
   wherein the illumination means comprises a second substrate parallel to the first substrate and bears multiple sources of the first type of radiation, one of the sources of the first type of radiation being positioned so as to face each of the passages.

2. The device according to claim 1, wherein each of the passages occupies positions of multiple contiguous missing pixels in the matrix.

3. The device according to claim 2, wherein the passages are uniformly distributed across the matrix.

4. The device according to claim 2, wherein the pixels that are contiguous with the passages are inactive.

5. The device according to claim 2, further comprising:
   components allowing the pixels to be controlled and read out,
   wherein the sensor comprises tracks connecting each of the pixels to the components, each track being routed along a row of pixels, and
   wherein, for the rows interrupted by passages among the pixels, the corresponding tracks are diverted around the passages via neighboring, uninterrupted rows.

6. The device according to claim 1,
   wherein the first substrate comprises a front face bearing the pixels, and a rear face opposite the front face, and
   wherein the sensor comprises a mask that is opaque to the first type of radiation, the mask being positioned on the rear face.

7. The device according to claim 1, wherein the first substrate and the second substrate are flexible.

8. The device according to claim 1,
   wherein the second substrate comprises a front face positioned so as to face the sensor, and
   wherein the illumination means comprise a mask that is opaque to the first type of radiation, the mask being positioned on the front face, the mask being apertured when facing the passages.

9. The device according to claim 1, wherein the illumination means is positioned away from the sensor.

10. The device according to claim 1, wherein each of the passages is an aperture passing through the first substrate.

11. The device according to claim 10, wherein the sources protrude with respect to the second substrate and are fitted into the passages.

12. The device according to claim 1, wherein each of the passages comprises a transparent zone of the first substrate.

13. A method for producing an image capture device comprising a sensor and an illumination means configured to emit a first type of radiation intended to illuminate an object in order to obtain an image thereof, the sensor comprising pixels that are sensitive to a second type of radiation dependent on the first type of radiation emitted by the illumination means, the pixels being arranged in an incomplete matrix having positions of at least one missing pixel, the sensor being formed on a first monolithic substrate comprising multiple passages that are transparent to the first type of radiation, each of the passages occupying the position of at least one missing pixel, the illumination means comprising a second substrate parallel to the first substrate and bearing multiple sources of the first type of radiation, one of the sources of the first type of radiation being positioned so as to face each of the passages, the method comprising:
   producing the sensor from the first substrate;
   producing the illumination means from the second substrate; and
   assembling the sensor and the illumination means.

* * * * *